United States Patent [19]
Sellers et al.

[11] Patent Number: 5,520,657
[45] Date of Patent: May 28, 1996

[54] METHOD AND DEVICE FOR VESSEL LOCATION CANNULATION UTILIZING A UNIQUE NEEDLE AND SYRINGE DEVICE

[76] Inventors: Jackie Sellers, 8700 Dawes Lake Rd., Mobile, Ala. 36619; Fred Brackett, 8255 Brackett La., Semmes, Ala. 36575

[21] Appl. No.: 104,346

[22] Filed: Aug. 9, 1993

[51] Int. Cl.$^6$ ............................................. A61M 5/00
[52] U.S. Cl. ...................... 604/191; 604/239; 128/762; 128/765
[58] Field of Search ........................... 604/191, 158, 604/194–197, 218, 221, 222, 231, 239, 232, 181, 82, 86, 87, 89, 20, 272, 110; 128/762, 765

[56] References Cited

U.S. PATENT DOCUMENTS

| Re. 32,974 | 7/1989 | Porat et al. | 604/208 |
|---|---|---|---|
| 3,749,084 | 7/1973 | Cucchiara | 128/762 |
| 4,245,654 | 1/1981 | Raitto | 128/765 |
| 4,313,440 | 2/1982 | Ashley | 604/191 |
| 4,957,637 | 9/1990 | Cornell | 210/782 |

FOREIGN PATENT DOCUMENTS

| 2229374 | 9/1990 | United Kingdom | 604/191 |
|---|---|---|---|

*Primary Examiner*—C. Fred Rosenbaum
*Assistant Examiner*—V. Alexander

[57] ABSTRACT

A syringe is disclosed having a large syringe housing which can be fitted with a large needle holder which in turn holds a large introducer needle. The introducer needle defines a passageway. A small seeker needle which is designed to fit within and through the passageway of the large introducer needle is attached by way of a small needle holder to a small syringe housing. A washer adapter attaches to the front of the small needle holder in order to have the small syringe housing move within a large syringe housing as a plunger for the large syringe housing. The small syringe housing in turn receives on one end a small syringe plunger which may define a small plunger lumen or chamber which can be used for transduction. Another embodiment has a modified needle having a port in the shaft within the syringe to allow sampling.

18 Claims, 4 Drawing Sheets

5,520,657

METHOD AND DEVICE FOR VESSEL LOCATION CANNULATION UTILIZING A UNIQUE NEEDLE AND SYRINGE DEVICE

BACKGROUND OF INVENTION

This invention applies to cannulation.

More particularly the invention applies to cannulation of the venous or arterial system but it is not limited to these sites.

PRIOR ART

Several devices for percutaneous sheathing introduction and several methods of cannulation are known in the art. Some of these involve transduction. Transduction is loosely defined as obtaining an electronic signal from a physical fluid pulse. The Seldenger technique is the most common method for introducing the catheter into a vein or artery. In this technique the vessel is located with a seeker needle (usually 22 g) and syringe and then an introducer needle is placed alongside in an attempt to access the same vessel. A wire is then placed through the needle and the needle is removed. The catheter is threaded into the vessel while being guided by the wire. Once the catheter is in place the wire is removed. One problem associated with the Seldenger technique, particularly with central venous cannulation, is that insertion is largely a learned technique which requires the maintenance of the angle of insertion of the introducer needle along the same plane as the seeker needle. Failure to maintain the same angle as the seeker needle may result in misplacement of the introducer needle or failure to locate the vessel.

The presented devices and associated techniques eliminate the need for two puncture sites by allowing for the insertion of a larger needle over a smaller needle while using the same needle—syringe unit. These devices and the associated techniques prevent unnecessary bleeding, allow the maintenance of the angle for insertion of the larger needle, and allow for appropriate insertion of the introducer needle.

Therefore it is a purpose of this invention is to provide an improved method of cannulation.

It is the further purpose of the invention to provide a novel device and method for insertion of a larger needle over a seeker needle.

A further purpose is to provide an improved method for sampling while performing cannulation and for maintaining a needle angle while performing cannulation.

These and other objects and advantages of the invention will become better understood hereinafter from a consideration of the specification with reference to the accompanying drawings forming part thereof, and in which like numerals correspond to parts throughout the several views of the invention.

SUMMARY OF THE INVENTION

The invention is an improved and safe method for cannulation utilizing a unique syringe device which allows for the insertion of a seeker and introducer needle as one unit. This provides the user with the ability to aspirate through both lumens independently or simultaneously. The preferred embodiment utilizes a unique and improved hypodermic syringe wherein a smaller (seeker) hypodermic syringe acts as a plunger for the larger (introducer) hypodermic syringe. The smaller syringe is specially modified to allow aspiration through a seeker needle and, if necessary, transduction of the same needle through the modified plunger of the small syringe. The large syringe barrel then acts as a unit with the introducer needle, advancing it over the seeker needle. This device allows one to use the small syringe and needle unit to inject local anesthetic, locate the correct vessel and aspirate with a seeker needle, transduce the needle holder in order to have the small syringe housing move within a large syringe housing as a plunger for the large syringe housing. The small syringe housing in turn receives on one end a small syringe plunger which may define a small plunger lumen or chamber which can be used for transduction. Another embodiment has a modified needle having a port in the shaft within the syringe to allow sampling.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein.

DETAILED DISCUSSION OF THE PREFERRED EMBODIMENT(S)

Figure 1:
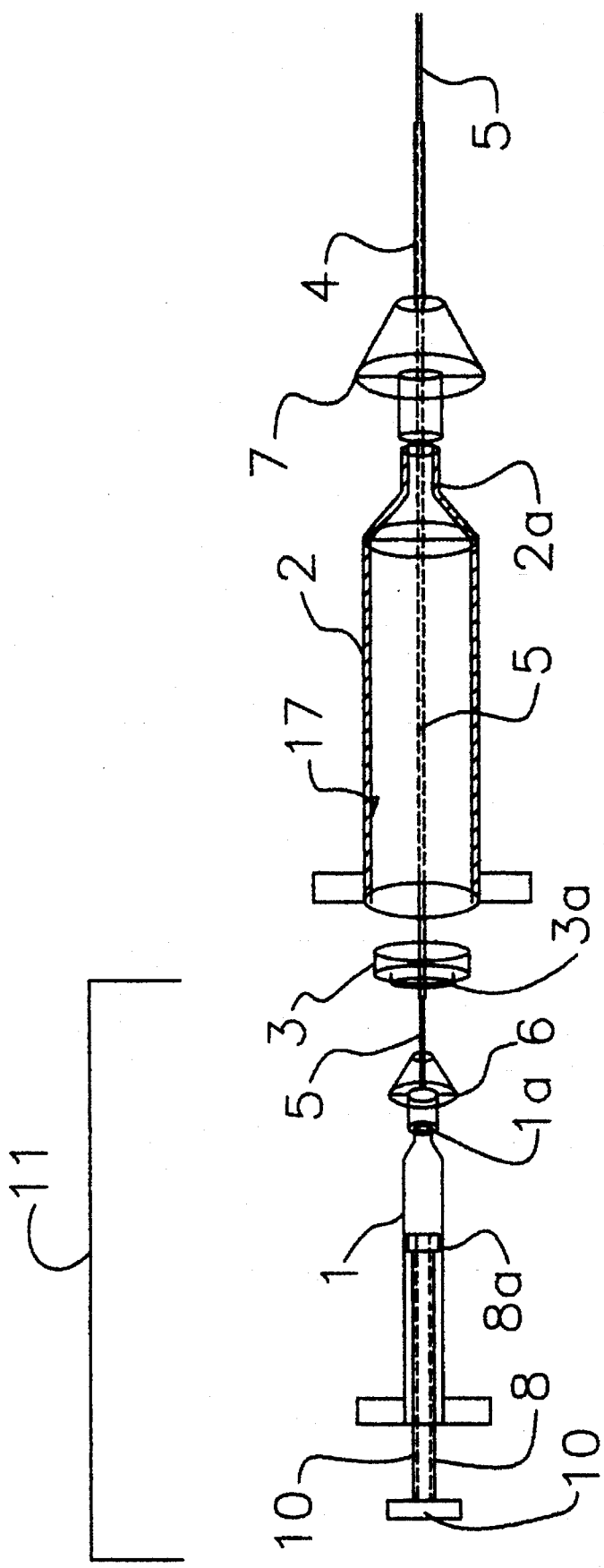
FIG. 1 is a plan view of the preferred embodiment of the invention.

The method of cannulation of a vessel and device described herein describes a process comprising the steps of (a) determining the angle of insertion;

(b) inserting a seeker needle 5 mounted on a housing barrel 2 at the determined angle of insertion into the vessel;

(c) transducing or aspirating the seeker needle 5 once it has accessed the vessel in question (either method being generally acceptable with transducing being more certain);

(d) maintaining the angle of the seeker needle 5 while inserting the introducer needle 4;

(e) inserting an introducer needle 4 over the seeker needle 5 while maintaining substantially the extent of penetration of the seeker needle 5;

(f) aspirating the seeker needle 5 after inserting the seeker needle;

(g) aspirating or transducing the introducer needle 4 after inserting the introducer needle 4 into the vessel over the seeker needle 5;

(h) removing the seal 3 from the plunger 11 to the housing barrel 2; and (i) removing the plunger 11.

As can best be seen by reference to FIG. 1, the invention in the preferred embodiment comprises a large syringe housing 2 which can be fitted with a large needle holder 7 which in turn, holds an introducer (large) needle 4. The introducer needle 4 defines a passageway 9. A seeker (small) needle 5 which is designed to fit within and through the passageway 9 of the large introducer needle 4 is attached by way of small needle holder 6 to the small syringe housing 1. A washer adapter 3 attaches to the front of the small needle holder 6 in order to have the small syringe housing move within the large syringe housing 1 as a plunger for the large syringe housing 2.

Figure 4:
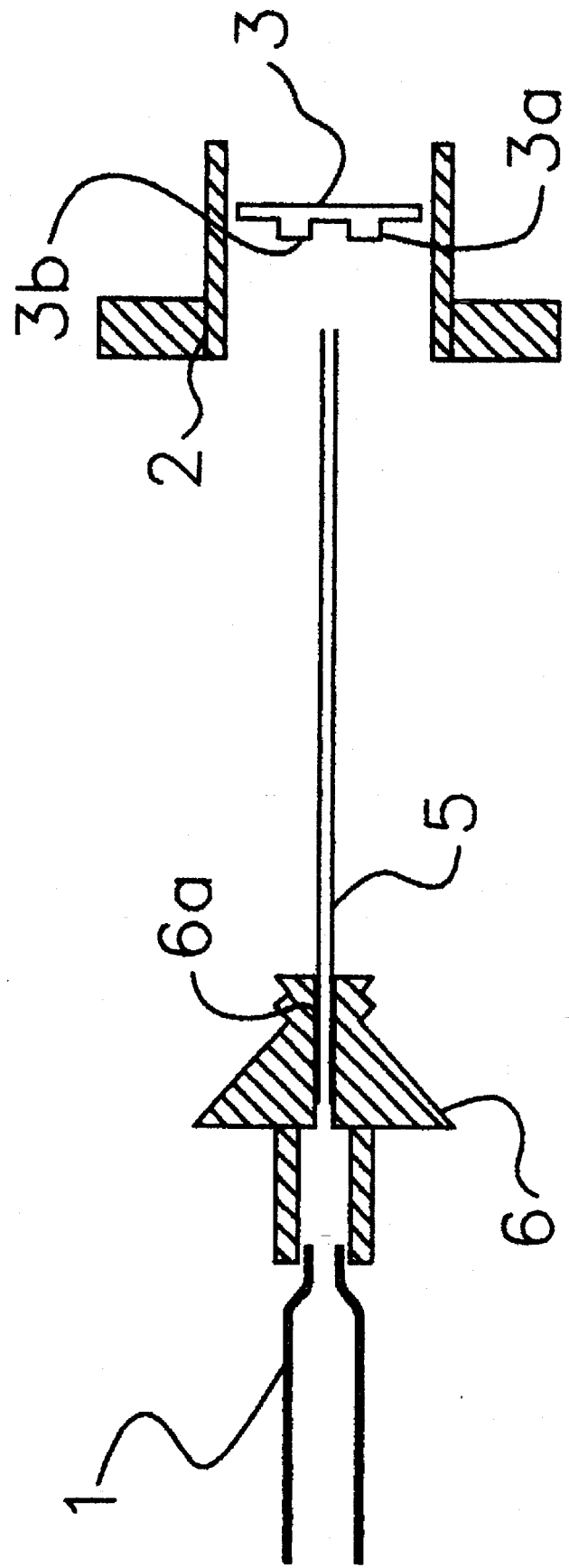
FIG. 4 is a detail of the modified washer seal of FIG. 3.

The large syringe housing 1 in turn receives on one end a small syringe plunger 8 which may define a small plunger lumen or chamber 10 which can be used for transduction. For transduction, a transducer needle (not shown) could pass through the lumen 10 of the small plunger 8 and then into the appropriate vessel. The front end 1a of the small syringe housing receives seeker needle holder 6 which holds the seeker needle 5. The seeker needle holder 6 holds a seal or washer 3. As shown on FIG. 4, the needle holder 6 may define threads 6a to screw into threads 3b defined on a bolt 3a attached to or formed out of an extension of washer 3. Similarly washer 3 may be made of suitable material so that it forms a solid puncturable unit which may reseal when the small needle 5 is removed.

The length of the small needle 5 is sufficient so that, when the large hypodermic plunger 11 comprised of the washer 3 and the syringe housing 1 is inserted a desired distance into the large housing 2, a sufficient length of the small needle 5 extends beyond the end of large needle 4 so that it may be used as a seeker needle 5.

The seeker needle 5 is properly inserted into the vessel (e.g. vein, artery or other fluid containing body of the body) into which the large needle 4 will ultimately be inserted using techniques known in the art.

Figure 2:
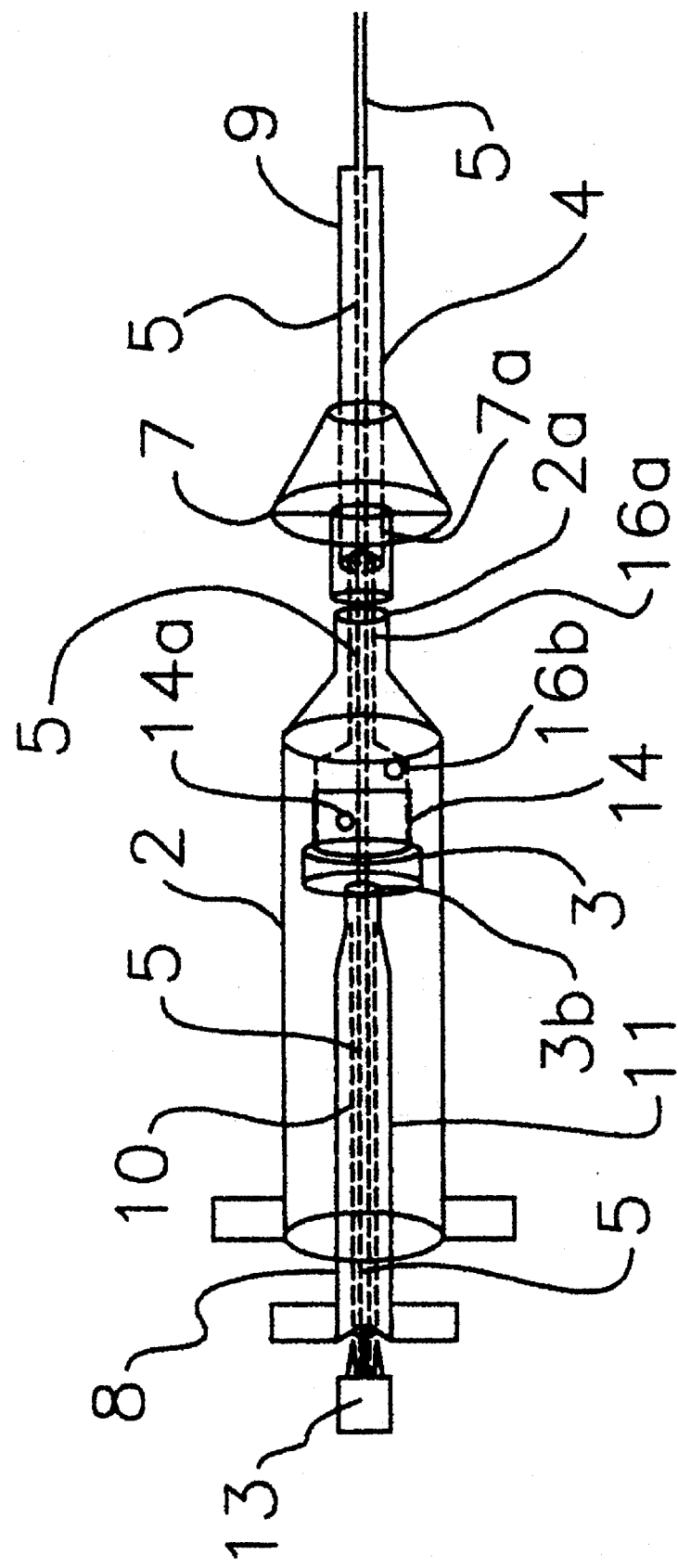
FIG. 2 is a alternate embodiment showing the use of a modified needle in place of the double syringe technique shown in FIG. 1.

Through either withdrawing plunger 11 to sample or through transduction utilizing opening 10 it can be determined that the seeker needle 5 is in the right location. For transduction it may be necessary to extend a current carrying wire into the opening 10 and contacting the needle 4 or 5 to be transduced. In FIG. 2 an extension of the seeker needle 5 serves this purpose. All this can be done while maintaining the angle of the seeker needle 5 because of the inclusion of the sampling syringe housing 1 in the plunger 11 of the large syringe housing 2 which holds the introducer needle 4.

When it is determined that the angle is correct and the seeker needle 5 is in the desired vessel, the large plunger housing 2 can be moved forward while the small plunger housing 1 is held in place. As the large housing 2 is moved forward and the plunger 11 is held in place, needle 4 is inserted over seeker needle 5 without moving the seeker needle 5 forward. The seeker needle 5 may be marked by color or otherwise to mark the length held within the patient to help insure the seeker needle 5 does not go further into the patient during insertion.

Continued aspiration or transduction is possible during this process to assure penetration is properly maintained.

When necessary, the large needle holder 7 can be removed from the housing 2 and the seeker needle completely withdrawn and replaced as necessary or the small plunger 11 may be removed with the needle 5 from the large housing 2 with or without the seal 3 to accomplish the same result.

Figure 3:
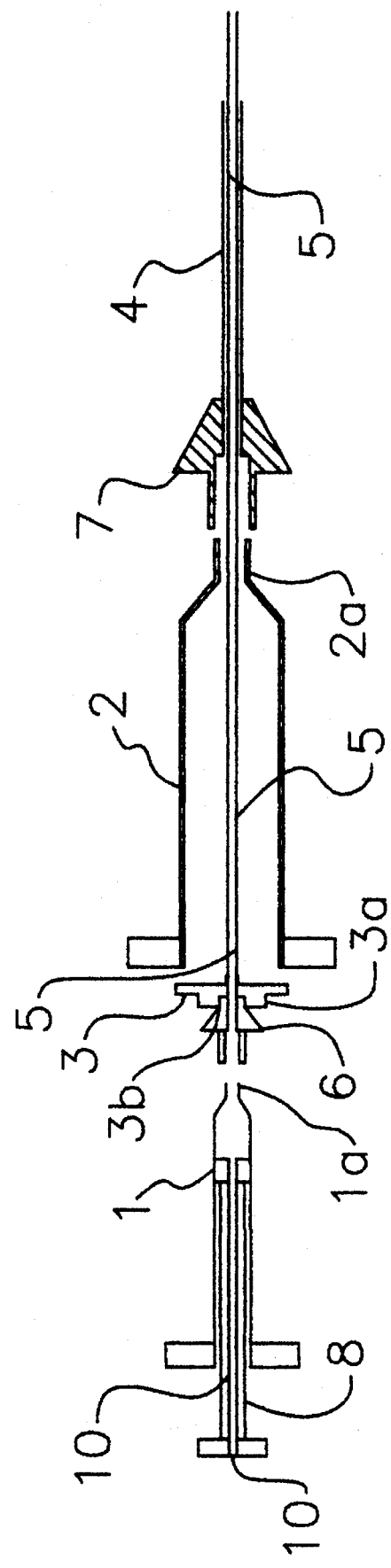
FIG. 3 is a cross section view of the invention of FIG. 1 having a modified washer seal.

A point is marked on the large housing 2 at which point the introducer needle 4 has been moved forward to completely cover the seeker needle 5. This is the point of full insertion. In the preferred embodiment this point may be preserved by a triangular stop 17 defined by housing 2 which is sloped to allow seal 3 to pass but presents a straight barrier to halt the backward movement of seal 3. As shown in more detail in FIG. 3 and 4, it may be desirable to remove all of the plunger 11 except the seal 3 from housing 2.

The invention in FIG. 1 comprises two plungers which advance or withdraw the two needles independently of each other to allow correct placement while allowing sampling or introduction of solution from either needle 4 or 5. This is all accomplished through one entry site instead of the most common technique now used in which there is more than one puncture site and the angle of insertion is often impossible to maintain due to anatomical movement and related difficulties.

This invention allows for less blood loss and a substantially lower number of puncture sites; thereby reducing the possibility of infection, nerve injury, pneumothorax, hematomas and other well known complications of venous or arterial cannulation.

The 22 gauge needle is used as the seeker needle 5 to find the vessel then you would use the 18 gauge or larger introducer needle 4 thread over the seeker needle 5.

Although the introducer needle 4 is typically a standard type of needle, this could easily be any type of device such as a fiber optic cable or housing for receiving fiber optics.

In the preferred embodiment shown in FIG. 1, the smaller needle 5 is a 22 gauge needle which would extend approximately one and one quarter inches beyond the 18 gauge tip as a seeker needle 5 when plunger 11 was fully inserted into Housing 2.

FIG. 2 shows an alternate embodiment with a single housing 2 and without housing 1. Luer lock 13 holds a seeker needle 5 within the plunger 11 and would come out of an opening 10 in the rear of the plunger 11. If the plunger 11 is held in place, the introducer needle 4 which is usually an 18 gauge needle may be inserted over the seeker needle 5 without changing the position of the seeker needle 5.

The seal or washer 3 of the large syringe plunger 11 may be designed to lock in place within housing 2 by a lock 17 between the housings. The seal 3 may be unscrewed from the needle housing 6. By having a hemostasis valve 15 defined by the seal 3 which valve closes the blood flow when the seeker needle 5 is withdrawn, the introducer needle 4 may be left in place while syringe housing 1 is removed leaving the seal 3 in place for testing purposes (e.g. checking for a spurt of blood into the housing 2. This blood spurt would be kept within housing 2 by the seal 3 which would close up when the seeker needle 5 was withdrawn).

The housing barrel 2 would be used to push the introducer needle 4 down into the seeker needle 5 when positive testing for venous blood by transduction or sampling confirms venous access. The cap or lock 13 covering the small plunger lumen 10 may be removed in order to transduce the needle 4 or 5 in the fashion similar to that discussed for the prior art.

FIG. 2 shows an embodiment with a single plunger 11. As shown in FIG. 2, the needle 5 may pass through the opening or lumen 10 in the plunger 11. A holding means or luer lock 13, usually a screw-on attachment to the rear of the plunger 8 acts to hold the small needle 5 in place. The needle 5 may be removed while the plunger 11 remains in place within the housing 2 by pulling out the luer lock 13 with the needle 5 attached.

The larger needle 4 is typically an 18 gauge needle. In the embodiment shown in FIG. 2 the 18 gauge needle attaches to the large housing 2 at the housing end 2a by way of the large needle holder 7.

The introducer needle 4 then fits over a secondary needle 16 which is slightly larger than the introducer needle 4 and is thereby designed to tightly receive the introducer needle 4. A needle opening 16b in an enlarged portion 16a of the secondary needle 16 serves to allow blood to be collected within the large housing as the plunger 11 is withdrawn creating a vacuum in the area between the front of the housing 16 and seal 3.

The secondary needle 16 is held by a secondary holder 17 to the plunger 11 in front of the plunger seal 3. A holder hole 17a defined by the secondary holder 17 allowing the secondary needle 16 to communicate with the interior of the housing 2 could be used for the same purpose and as an alternative to the needle opening 16b.

In the alternative embodiment of FIG. 2, the seeker needle 5 would need to be long enough to fit through the plunger 11 and barrel 2 and 18 gauge introducer needle 4 in order to be used as a seeker.

In the embodiment shown in FIG. 2 the introducer needle 4 can be separated by removing the introducer needle holder 7 so that the housing 2 can be removed after insertion.

We claim:

1. A device for cannulation of a vessel comprising:

(a) a seeker needle;

(b) an introducer needle defining a passageway for receiving the seeker needle at an inner end thereof, the seeker needle extending though the passageway and outwardly from an outer tip end of the introducer needle;

(c) a large syringe housing;

(d) means for connecting the introducer needle to the large syringe housing; and (e) means for forming a large syringe plunger, said plunger forming means comprising a small syringe housing having a front end within the large syringe housing and a back end extending out of the large syringe housing, holding means for attaching the seeker needle to the front end of the small syringe housing, and means for providing a seal between the large syringe housing and the plunger forming means;

wherein said introducer needle is movable forward over the seeker needle while the seeker needle is inserted to a desired degree and a desired angle in a vessel, and the small syringe housing is slidably movable within the large syringe housing to allow at least partial withdrawal of the seeker needle through the introducer needle without affecting the position of the introducer needle after insertion of the introducer needle into the vessel over the seeker needle.

2. The device of claim 1 wherein the seal providing means comprises a washer having an inner circumference and an outer circumference and wherein the washer fits over the holding means and forms a substantially water tight seal between the inner circumference of the washer and the holding means and a substantially watertight seal between the outer circumference of the washer and the large syringe housing.

3. The device of claim 1 wherein the holding means further comprises a seeker needle holder mounted onto the front end of the small syringe housing.

4. The device of claim 1 further comprising means for aspirating the introducer needle.

5. The device of claim 4 wherein the introducer needle aspirating means comprises said plunger forming means cooperating with the large syringe housing.

6. The device of claim 5 further comprising means for aspirating the seeker needle.

7. The device of claim 6 wherein the seeker needle aspirating means comprises a small plunger fitting within the small syringe housing, and wherein the seeker needle is aspirated before the introducer needle.

8. The device of claim 1 further comprising a transducer means for transducing the seeker needle.

9. The device of claim 8 wherein the transducing means comprises a small plunger fitting within the small syringe housing, said small plunger defining a current means for connecting a transducer/plunger lumen to the seeker needle, and wherein the seeker needle is transduced before the inducer needle.

10. The device of claim 1 wherein the device further comprises a means for maintaining the angle of the seeker needle while the introducer needle is inserted over the seeker needle.

11. The device of claim 1 further comprising a means for maintaining the extent of penetration of the seeker needle as the introducer needle is inserted over the seeker needle.

12. The device of claim 1 wherein the small syringe housing further defines an attachment means for releasably attaching to the seal providing means so that the seal providing means may be left in place within the large syringe housing when the small syringe housing is removed with the seeker needle.

13. The device of claim 12 wherein the attachment means further comprises a male set of threads on the holding means and a cooperating set of female threads defined by the seal providing means.

14. The device of claim 13 wherein the seal providing means further defines a flow means for controlling blood flow through the introducer needle.

15. The device of claim 14 wherein the flow means further comprises a hemostasis valve defined by the seal providing means.

16. The device of claim 12 further comprising a locking means for locking the position of the seal providing means within the large syringe housing.

17. The device of claim 16 wherein the locking means further comprises a triangular notch defined by the large syringe housing presenting a sloping surface with the slope beginning at the point closest to the opening of the large syringe housing for receiving the plunger forming means and presenting at the desired location for locking the position of the seal providing means a straight wall going down from the sloping end.

18. The device of claim 1 wherein the small syringe housing is slidably removable from the large syringe housing to allow complete withdrawal of the seeker needle through the introducer needle.

* * * * *